US012642500B2

(12) United States Patent
Arthur et al.

(10) Patent No.: US 12,642,500 B2
(45) Date of Patent: Jun. 2, 2026

(54) NON-DESTRUCTIVE X-RAY IMAGING DETECTOR UTILIZING ARTIFICIAL INTELLIGENCE TO OPTIMIZE SYSTEM EFFICIENCY

(71) Applicants: Randall Arthur, Campbell, CA (US); Anthony E. Dimalanta, San Jose, CA (US); Nguyen Phuoc Luu, Los Gatos, CA (US); Paul R. Overmyer, Sunnyvale, CA (US); Chinlee Wang, Saratoga, CA (US)

(72) Inventors: Randall Arthur, Campbell, CA (US); Anthony E. Dimalanta, San Jose, CA (US); Nguyen Phuoc Luu, Los Gatos, CA (US); Paul R. Overmyer, Sunnyvale, CA (US); Chinlee Wang, Saratoga, CA (US)

(73) Assignee: X-Scan Imaging Corporation, San Jose, CA (US)

( * ) Notice: Subject to any disclaimer, the term of this patent is extended or adjusted under 35 U.S.C. 154(b) by 204 days.

(21) Appl. No.: 18/752,791

(22) Filed: Jun. 25, 2024

(65) Prior Publication Data

US 2025/0004147 A1 Jan. 2, 2025

Related U.S. Application Data

(60) Provisional application No. 63/524,132, filed on Jun. 29, 2023.

(51) Int. Cl.
| | |
|---|---|
| *A61B 6/58* | (2024.01) |
| *G01N 23/04* | (2018.01) |
| *G01T 1/20* | (2006.01) |
| *G01T 1/24* | (2006.01) |

(52) U.S. Cl.
CPC ............ *A61B 6/586* (2013.01); *G01N 23/04* (2013.01); *G01T 1/20* (2013.01); *G01T 1/244* (2013.01)

(58) Field of Classification Search
CPC .......... G01T 1/244; G01T 1/20; A61B 6/586; G01N 23/04
See application file for complete search history.

(56) References Cited

U.S. PATENT DOCUMENTS

| | | | | |
|---|---|---|---|---|
| 5,006,713 A * | 4/1991 | Miller | ....................... | G01T 1/20 250/361 R |
| 5,594,819 A * | 1/1997 | Narendran | ............. | G01B 11/18 385/12 |
| 11,103,207 B1 * | 8/2021 | Singh | .................... | H01J 35/025 |
| 2011/0096904 A1* | 4/2011 | Tseng | ........................ | G01T 1/20 378/62 |
| 2017/0115406 A1* | 4/2017 | Li | ........................ | G01T 1/20181 |
| 2020/0108278 A1* | 4/2020 | Friedman | ............ | G01T 1/20188 |

\* cited by examiner

*Primary Examiner* — Chih-Cheng Kao

(57) ABSTRACT

A high-energy x-ray camera with radiation-hardened fiber optic faceplate to protect its sensor chip from radiation damage, a field-replaceable scintillator which degrades under radiation. A signal and SNR monitoring system and method to optimize the scintillator replacement schedule.

10 Claims, 7 Drawing Sheets

501

502

20

503

700

790

| Processor Unit 710 | | Output Devices 750 |
| Main Memory 720 | | User Input Devices 760 |
| Mass Data Storage 730 | | Graphics Display System 770 |
| Portable Storage Device 740 | | Peripheral Devices 780 |

NON-DESTRUCTIVE X-RAY IMAGING DETECTOR UTILIZING ARTIFICIAL INTELLIGENCE TO OPTIMIZE SYSTEM EFFICIENCY

CROSS REFERENCE TO RELATED APPLICATIONS

This application claims a priority filing date from U.S. Provisional Application No. 63/524,132, filed Jun. 29, 2023, and incorporates by reference the disclosures therein.

FIELD OF THE INVENTION

The present invention pertains generally to the field of solid-state image sensors, and more particularly is a method of optimizing performance of high-energy x-ray detectors.

BACKGROUND OF THE INVENTION

Non-Destructive Testing (NDT) is utilized in many commercial applications, and is a vital aspect of quality assurance in various industries. The primary purpose of NDT is to ensure that products are free from defects and contamination. X-ray or radiographic imaging is a widely used modality in NDT that enables thorough inspection of the subject products. However, there are challenges associated with NDT, one of which is radiation hardness in high-speed in-line inspection applications.

NDT techniques, including x-ray imaging, are employed by industries to meticulously inspect products for defects and contamination. X-ray radiography allows for the detection of internal defects such as cracks, voids, and inclusions, which might compromise the product's integrity. By identifying these issues during the inspection process, manufacturers can take corrective actions and ensure that only high-quality, defect-free products reach the market.

Time-Delay Integration (TDI) is an imaging technology used in high-speed non-destructive testing (NDT) inspection processes. TDI enables the handling of high line rates, improving signal levels, and enhancing the efficiency of the inspection. By capturing multiple exposures of the inspected object as it moves across the detector, TDI allows for accurate imaging even at high speeds, contributing to faster and more effective quality control screening.

Specifically, TDI sensors increase signal levels in high-speed line-scan applications where the integrated input light signal is very low. In a normal line scan application, one way to increase the integrated input light signal is to reduce the scan speed and thus increase the integration time. However, this measure will necessarily reduce the inspection throughput. Using TDI sensors allows the line-scan detector system to increase the light signal without sacrificing the scan speed. A high-performance TDI sensor is typically implemented using a Charge-Coupled Device (CCD). A CCD is a semiconductor device that uses an array of capacitors to store charge. When light strikes a CCD pixel, it creates an electrical charge that is stored in the corresponding capacitor. The CCD then reads out the charge from each pixel in sequence, which creates an image. The CCD has multiple stages, or rows, of pixels. As the object being inspected moves across the detector, the signal charge from each pixel is transferred to the next row of pixels. This process is repeated until the object has passed completely through the detector. By the time the object reaches the end of the detector, the signal charge has been multiplied by the number of rows in the CCD, resulting in a significant increase in the signal level.

A CCD device used in a high performance TDI sensor has N stages and M columns, each capable of converting light to charge. In operation, the first stage of the CCD integrates the light signal within one integration time unit. The signal charge will then transfer from the first stage to the second stage of the CCD while the specimen under scan moves from the first stage to the second stage of the CCD in synchronization with the movement of the signal charge. The second stage of the CCD will then integrate signal charge during the second integration time for the same specimen. As a result, at the end of the second integration time, the signal charge at the second stage CCD will be twice the signal charge as compared to the charge the CCD receives from the first stage. The signal charge of the second stage will then move to the third stage in synchronization with the movement of the specimen being examined. Again, as with the second stage, the third stage of the CCD integrates the light signal it generates with the signal it receives from the second stage. This process repeats until the specimen reaches the final Nth stage of the CCD. At this point, the light signal has been multiplied N times. An output CCD shift register then reads out the M pixels of the signal in sequence.

While TDI detectors offer significant advantages in high-speed NDT inspection, TDI detectors are still susceptible to x-ray radiation damage. When inspecting thicker products, higher x-ray energies are required to penetrate the material and obtain clear images. This is crucial in industries such as aerospace, automotive, power generation, and various other manufacturing processes, where components and structures can vary in thickness. By utilizing x-ray sources with adequate energy levels, users of NDT systems can ensure that even the thickest products are thoroughly inspected, thereby leaving no room for undetected defects or contamination.

While x-ray imaging is highly effective in NDT, CCDs, the detectors used in the process, are susceptible to radiation damage, particularly in high-speed in-line inspection applications with long or continuous shifts. The prolonged exposure to x-rays can degrade the performance of the CCDs, leading to reduced image quality and potentially compromising the accuracy of defect detection. This presents a significant challenge in maintaining the reliability and longevity of CCD-based NDT systems.

Efforts have been made to address the issue of radiation hardness in CCD-based NDT systems. Various methods, such as employing radiation-hardened CCDs, implementing shielding techniques, and optimizing exposure times, have been used to mitigate radiation damage. However, these measures are often insufficient to completely eliminate the detrimental effects of extended radiation exposure. Further research and technological advancements are necessary to develop more robust and resilient CCDs capable of withstanding the rigors of high-speed NDT inspection.

Non-Destructive Testing, particularly systems utilizing x-ray imaging, plays a crucial role in ensuring product quality by detecting defects and contamination. CCD TDI technology enables high-speed inspection, enhancing the efficiency of quality control processes. However, the challenges associated with radiation hardness in CCD-based NDT systems pose a significant concern. Continued research and development efforts are essential to overcome these challenges, ensuring that NDT remains a reliable and effective tool for quality assurance in industries worldwide.

DETAILED DESCRIPTION OF THE INVENTION

Especially in a production environment, it is essential that inspection detector devices have a long lifespan with minimal downtime for maintenance. This is especially true for high-energy CCD TDI devices, which are used to inspect products for defects in harsh environments.

Figure 1:
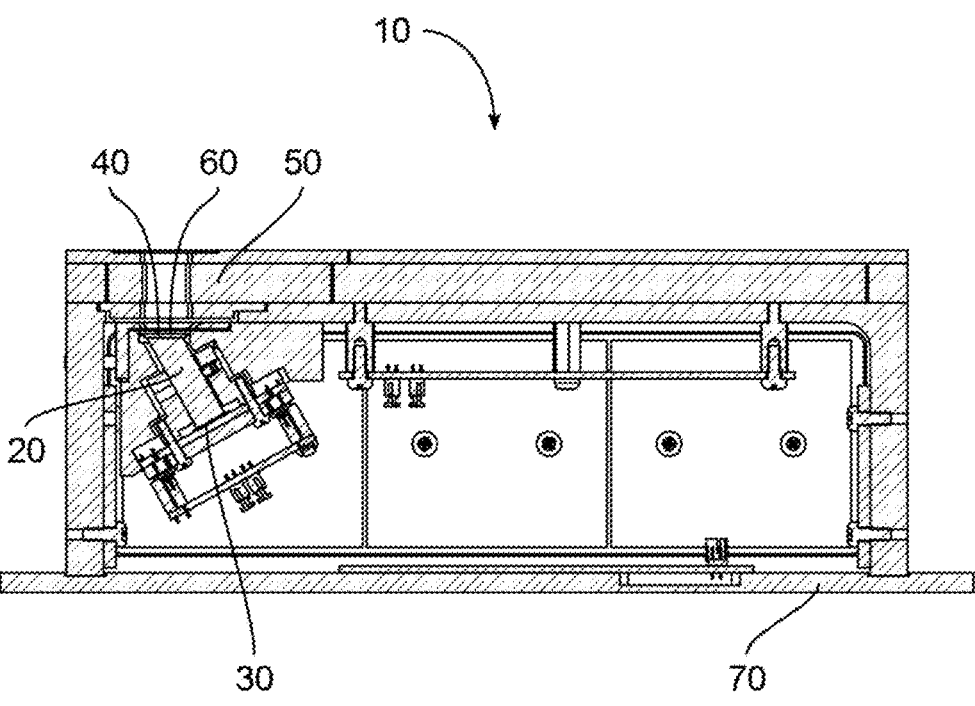
FIG. 1 shows a cross section of a CCD TDI imaging device.
Figure 2:
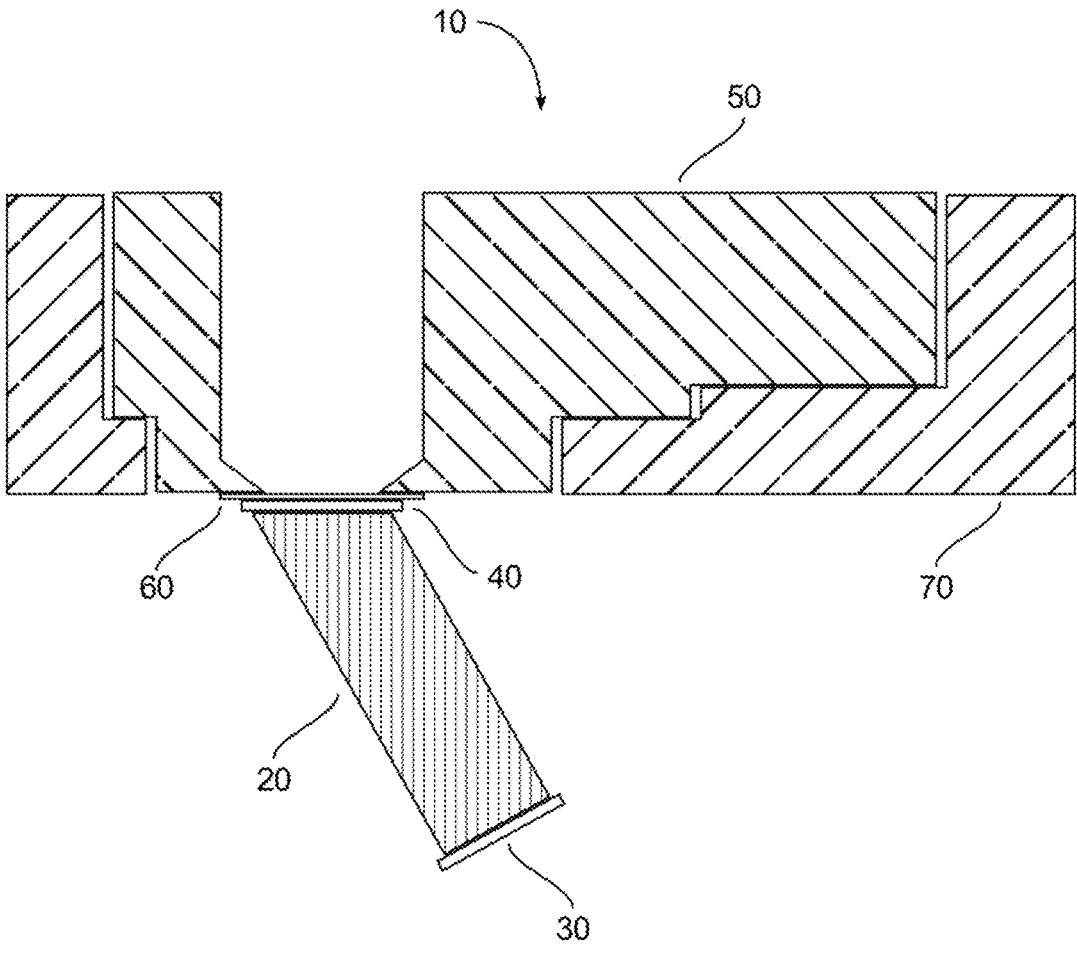
FIG. 2 is another sectional view showing components of the CCD TDI imaging device.
Figure 3:
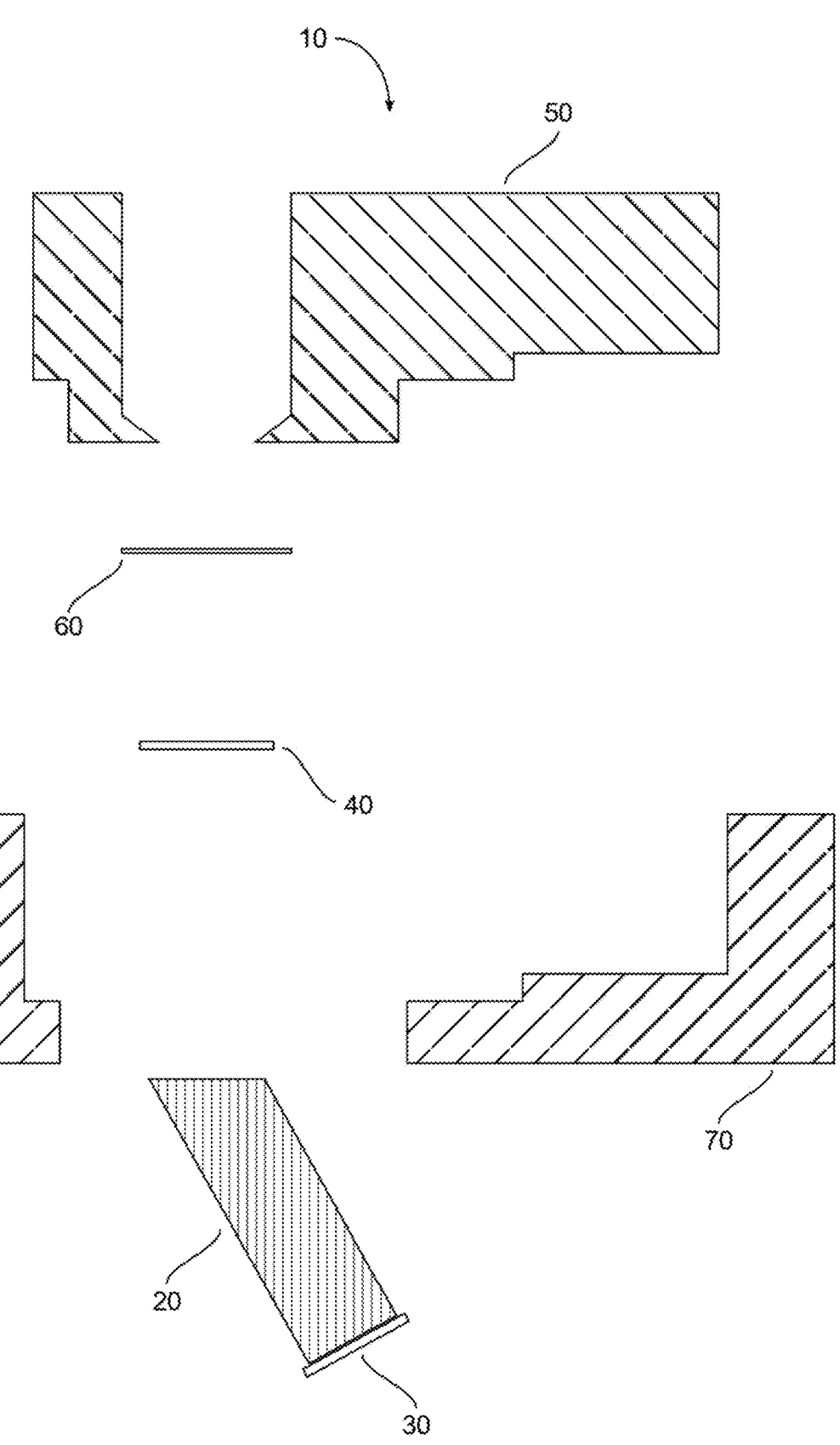
FIG. 3 is an exploded view of the components shown in FIG. 2.

FIGS. 1-3 illustrate a CCD TDI device 10 constructed according to the present disclosure. The device 10 includes a fiber optic faceplate (FOP) 20 that is mounted on a sensor 30. The FOP is configured to protect the sensor 30 from radiation damage. The FOP 20 is typically made from a radiation-hardened fiber optic material.

A scintillator 40 is mounted on an end of the FOP 20 opposite the sensor 30. The scintillator 40 converts x-rays into visible light. The visible light is then transmitted through the FOP 20, and is then detected by the sensor 30. Access to the FOP 20 and the sensor 30 is provided via a window 50 and a cover 60. The elements of the device are contained within an enclosure 70. The FOP 20 is positioned off-axis so that the sensor 30 is not in the direct path of the x-ray radiation, but under radiation shielding built into the camera enclosure.

A normal FOP 20 is a rectangular block. The block needs to fit over the active imaging area of the sensor chip 30, but not block things like the electrical wire bonds. The thickness should be enough to block x-rays, and can range from around 3 mm to 25 mm for typical x-ray energy ranges. The FOP 20 can also be mounted on-axis (as opposed to the above described off-axis) on the front of the CCD silicon sensor. The FOP 20 is made from a radiation-hardened fiber optic material, which can protect the CCD silicon structure if it absorbs a sufficient percentage of the radiation. The use of a flat, rectangular, on-axis FOP can provide several advantages over the use of an off-axis FOP. First, the on-axis orientation of the FOP can reduce the amount of light that is lost due to reflection and scattering. This can improve the image quality of the CCD TDI device. Second, the flat, rectangular shape of the FOP can provide a more uniform light distribution to the CCD sensor. This can also improve the image quality of the CCD TDI device. Third, the less complicated shape of the FOP can simplify the design of the CCD TDI device. This can reduce the cost of the CCD TDI device and make it easier to manufacture.

While various types of sensors 30 may be implemented in the systems, a CCD silicon sensor 30 is often utilized. The CCD sensor 30 can be assembled as tiled chips on a printed circuit board (PCB). Additional PCBs provide power, driver signals, amplification, analog-to-digital conversion, and interfacing to a computer that performs the data acquisition of the images.

Another option for the sensor 30 is a CMOS sensor. The use of a CMOS sensor can provide several advantages over the use of a CCD sensor. CMOS sensors are typically less expensive than CCD sensors, and they can also be manufactured in larger sizes. Additionally, CMOS sensors have a higher dynamic range than CCD sensors, which can be beneficial in applications where there is a wide range of light levels.

Cumulative X-ray radiation can be damaging to the CCD sensors 30, potentially causing performance degradation which leads to premature failure of the device 10. The FOP 20 provides protection to the silicon structure of the CCD sensor 30. The FOP 20 acts as a radiation shield by absorbing and attenuating the incoming x-ray radiation. The microscopic fibers within the FOP 20 are designed to have a high-density and a high atomic number, which enables them to effectively absorb and scatter x-ray photons. The absorption and scattering of the x-ray photons prevents the radiation from reaching the sensitive CCD 30 surface, thereby reducing the risk of radiation-induced damage. By providing a physical barrier against x-ray radiation, the FOP 20 ensures the long-term reliability and functionality of the CCD sensor 30 in CCD devices in environments where x-ray exposure is present. These environments include not only non-destructive testing, but also medical imaging and security applications.

However, FOPs can themselves degrade over time due to "browning centers". Browning centers are defects that occur when the fiber optic material of an FOP is exposed to ionizing radiation, leading to color centers that absorb and scatter light. Radiation-hardened FOPs are specifically engineered to prevent the formation of browning centers, which can degrade the transmission of light through the faceplate. To mitigate the formation of browning centers, radiation-hardened FOPs are manufactured using materials with high resistance to radiation-induced coloration. These materials typically have a low level of impurities and are carefully selected for their ability to withstand ionizing radiation without significant degradation. Additionally, advanced fabrication techniques, such as purification processes and controlled manufacturing environments, are employed to minimize impurities and ensure the uniformity and quality of the FOP 20. By preventing the formation of browning centers, radiation-hardened FOPs maintain the integrity of light transmission in an optical system. This enables users to create reliable and high-performance optical systems in radiation-prone environments.

The scintillator 40 is constructed from materials commonly used in radiation detection and imaging systems due to the ability of those materials to convert incident radiation, such as x-rays, into visible light or other detectable signals. However, scintillators can experience degradation in emission performance when exposed to x-ray radiation. This degradation occurs due to a phenomenon known as radiation damage.

A radiation resistant scintillator option is using GOS(Tb) or terbium-doped gadolinium oxysulfide ($Gd_2O_2S$). GOS (Tb) is a high-performance scintillator that is known for its high light yield, good energy resolution, and resistance to radiation damage. GOS(Tb) can help to extend the lifetime of the CCD TDI device by providing a high-performance scintillator that is resistant to radiation damage. The use of a GOS(Tb) scintillator can also help to improve the performance of the CCD TDI device by reducing afterglow compared to CsI(TI).

Another alternative scintillator material is GOS(Pr) or praseodymium-doped gadolinium oxysulfide. GOS(Pr) has advantages over GOS(Tb) in terms of faster decay times and lower afterglow, but at the cost of lower light yield.

When x-ray radiation interacts with a scintillator material, it can cause various types of damage at the atomic and molecular level. One of the primary mechanisms causing the damage is ionization, where x-ray photons transfer energy to the atoms or molecules of the scintillator, resulting in the creation of ionized species and free electrons. These ionized species and free electrons can lead to localized defects within the scintillator material.

Another mechanism that can cause degradation of the scintillator material is atomic displacement, where the high-energy x-ray radiation displaces atoms from their proper lattice positions, causing lattice defects or vacancies. These displaced atoms can disrupt the desired regular arrangement of atoms within the scintillator, affecting the crystal structure and properties of the scintillator material. The extent of degradation in scintillator emissions is a function of various factors, including the radiation dose, radiation energy, scintillator composition, and scintillator material properties. High doses of x-ray radiation or prolonged exposure can accelerate the degradation process of the scintillator and result in a decrease in the emission intensity, efficiency, and resolution of the scintillator. While there are some mitigation measures against scintillator degradation, radiation-induced degradation is inevitable and is significant within typical device lifetimes for the most popular high-performance scintillator materials.

One way to extend the lifetime of a CCD TDI device is to use a replaceable scintillator 40. The replaceable scintillators 40 can be easily swapped out in the field, which minimizes downtime and keeps the inspection system running smoothly. To replace the scintillator 40, the window 50 and cover 60 are removed to expose the scintillator 40. The scintillator 40 is removed from the FOP 20 and a replacement scintillator 40 is installed.

Figure 4:
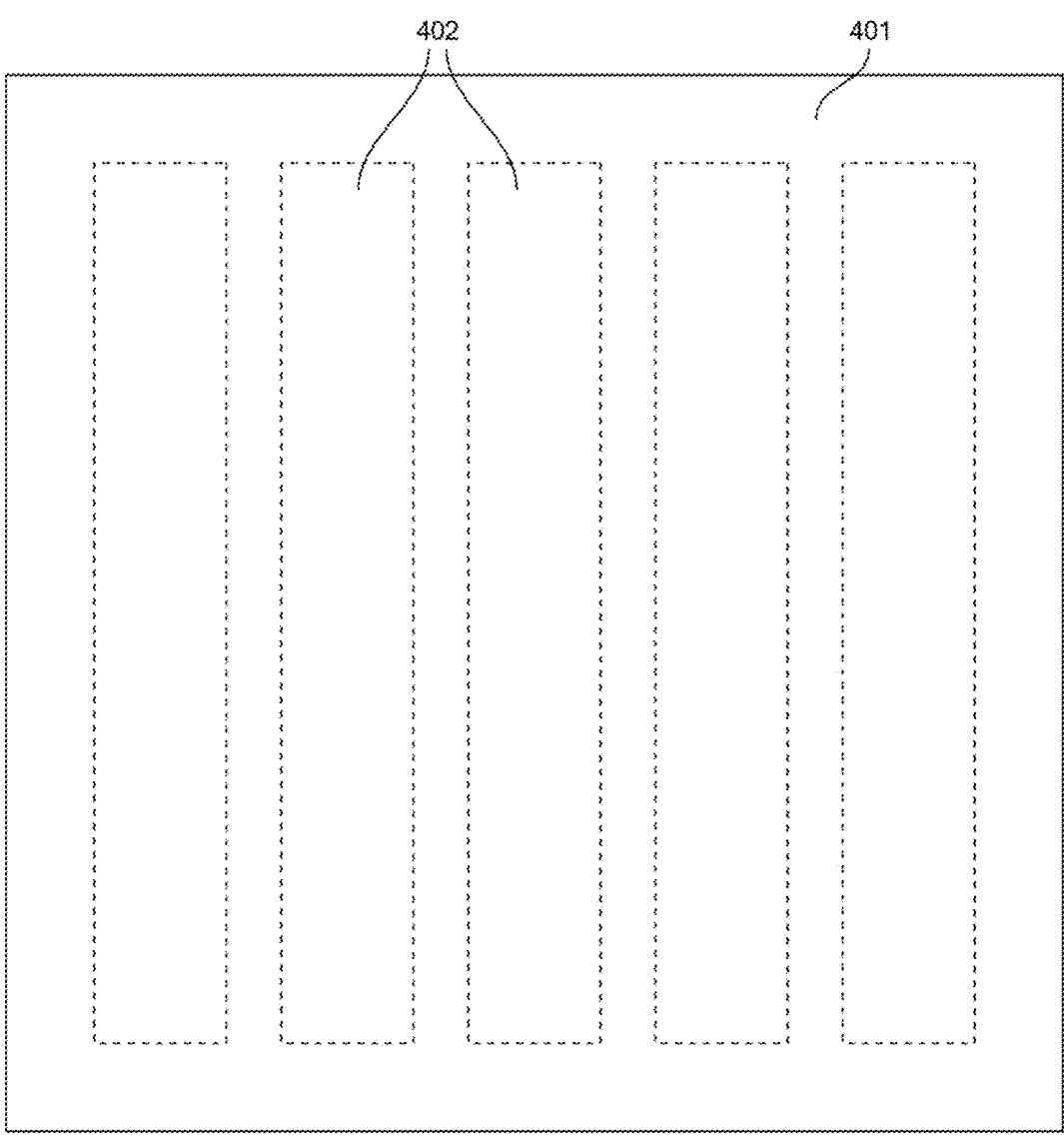
FIG. 4 shows a scintillator plate with multiple exposure segments.

In order to minimize downtime when replacing scintillator 40 units, a scintillator plate 401 that has multiple scintillator segments 402 can be installed in the device 10. An exemplary scintillator plate 401 with multiple segments 402 is illustrated in FIG. 4. Utilizing a scintillator plate 401 with multiple segments 402 reduces the time required for replacement of the scintillator 40 to a negligible amount. The multiple segments 402 of the scintillator plate 401 match the size of the x-ray window 50. Initially, a first segment 402 is aligned to be exposed to radiation by aligning a first segment 402 with the x-ray window 50. When the first segment 402 has aged to its limit, the plate 401 is repositioned so that a second one of the segments 402 is aligned with the window 50. This process is repeated until all the segments 402 on the plate 401 have been utilized.

Figure 5:
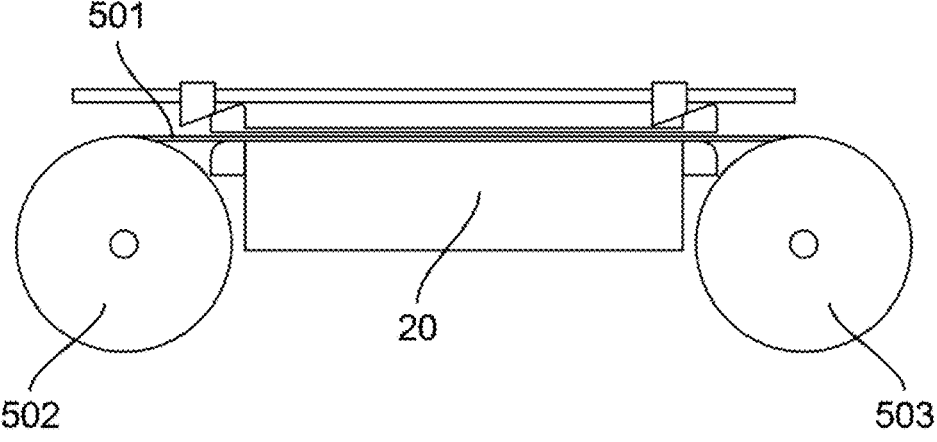
FIG. 5 shows a reel-to-reel scintillator utilized in various embodiments of the present disclosure.

Various embodiments of CCD TDI devices employ a real-to-reel constructions as illustrated in FIG. 5. In embodiments employing the reel-to-reel concept, scintillator material is deposited or formed onto or into a thin, flexible scintillator film 501. The scintillator film 501 is wound onto a first supply reel 502. The film 501 is then fed to a second take-up reel 503. In this manner, the film 501 can be advanced in stages across the FOP 20. The scintillator film 501 is transferred from reel 502 to reel 503 in a fashion akin to that of an audio cassette tape. This operation is easily automated, thereby further reducing the need for system downtime to replace the scintillator.

Figure 6:
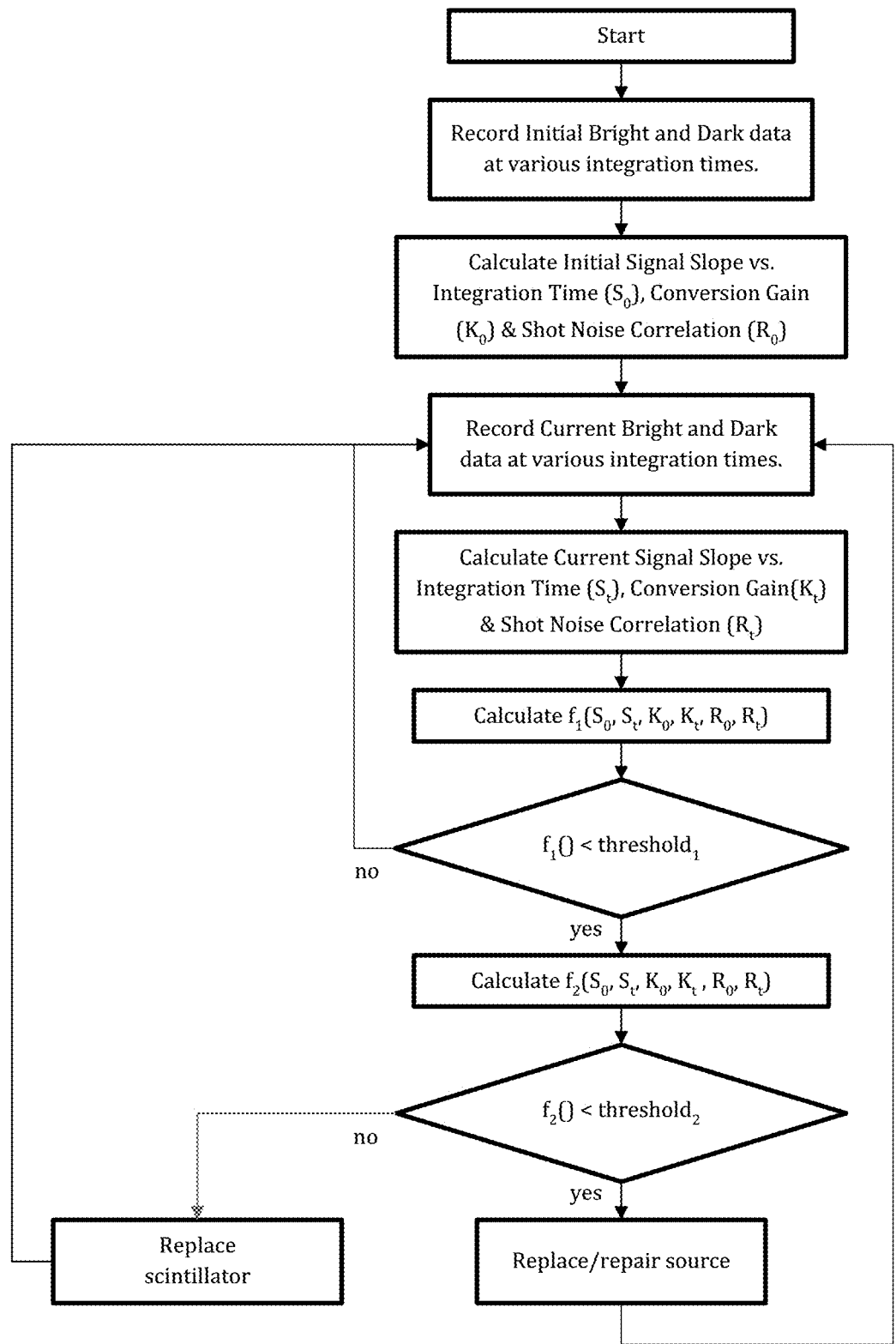
FIG. 6 is a flowchart of a method to optimize the replacement or repair of components of the CCD TDI imaging device.

A key to the operation of the CCD TDI system 10 is the real time monitoring of signs of degradation in the system and the use of artificial intelligence (AI) to predict when various components must be replaced. The data collection method and the component replacement algorithm are illustrated in FIG. 6.

The CCD TDI system 10, includes the fiber optic faceplate 20 and the replaceable scintillator 40. Those elements operate in conjunction with an x-ray source and an x-ray detector. The monitoring methodology includes mechanisms to monitor an open-air x-ray signal from the x-ray source, and an attendant open-air signal-to-noise ratio (SNR) of the CCD TDI system 10. The open-air x-ray signal is the x-ray signal measured when there is no material between the x-ray source and the x-ray detector. This means that the x-rays are not absorbed or scattered by any material, and they travel in a straight line from the source to the detector.

The SNR is one measure of the quality of the signal that is being detected by the CCD sensor 30. A higher SNR indicates a greater signal quality, while a lower SNR indicates a lesser signal quality. If the open-air SNR of a CCD TDI detector begins to degrade, it is an indication that the radiation source is losing flux, and is therefore producing fewer x-ray photon quanta directed at the x-ray detector. When SNR is dominated by x-ray photon shot noise (a form of quantum noise related to the statistics of photon counting), the number of quanta is proportional to the arithmetic square of the open-air SNR. This means that the source is emitting less radiation, which ultimately will lead to a decreased signal and the attendant SNR that is being captured by the CCD sensor. When the SNR is reduced sufficiently, the imaging system fails to meet its imaging requirements. When this happens, the x-ray source should be replaced or repaired.

However, if the open-air SNR remains constant while the open-air signal is dropping, it is an indication that the detector is starting to degrade, which means that the scintillator 40 is starting to lose its sensitivity. In this case, the scintillator 40 should be replaced. When the square of the open-air SNR is proportional to the number of quanta, the ratio of the open-air signal to the square of the open-air SNR is proportional to the detector sensitivity or responsivity. Since the scintillator degradation is expected to be the most significant factor in detector effectiveness, this ratio is used as an indicator of the condition of the scintillator.

By monitoring the open-air signal and SNR of the CCD TDI system 10, and utilizing this data, an optimal replacement schedule can be predicted, as is illustrated in FIG. 6. The methodology enables the user to predict when the system will fail to meet imaging requirements. The method for determining the optimal replacement schedule for the scintillator involves the collection of the open-air signal and SNR data over time. The method uses this data to set up alerts based on changes in the signal and SNR. Readings of the signal and SNR are stored in a database for analysis and extrapolation. This methodology can be used to predict when the scintillator will fail and to schedule maintenance to replace it before it fails, which minimizes downtime and its impact on the production system.

FIG. 6 graphically illustrates the method. The first step of the method is recording bright and dark data at multiple integration times. Bright data refers to data collected from the detector when the x-ray source is turned on. Dark data is the output from the detector when the x-ray source is turned off. The measurements can be done automatically and directly recorded in data storage means of the system. Alternatively, the measurements can be made manually, then input into the system. This data enables the user to calculate an initial signal slope (measuring the variation of the signal versus integration time), conversion gain, and shot noise correlation.

The method then loops the data collection steps, recording data for the signal slope, the conversion gain, and the shot noise correlation at each measurement point. The successive measurement data is compared to a threshold value established by the user. If the threshold for a given characteristic is met by one of the measurements, then corrective action is indicated. As an example, if any or all of the signal slope S were to decrease to say 30 percent of its initial value, and/or the conversion gain K moves plus or minus 15% of its initial value, and shot noise correlation R is less than 0.9, then the most recent data would be checked to confirm that the curve fit is still valid. If the slope were to fall but the conversion gain remains constant, the method might suggest that the x-ray source be repaired or replaced. If both the slope and the gain exceed the threshold value, then the scintillator may be replaced.

A machine code, such as a Python Code, can be used to measure and monitor the data collected in the system. The code can be fed initial data as a starting point, then successive measurement points to teach the code to determine if degradation has occurred in the system components. Successive data points are fed to the code to optimize and monitor the threshold values of the system.

Figure 7:
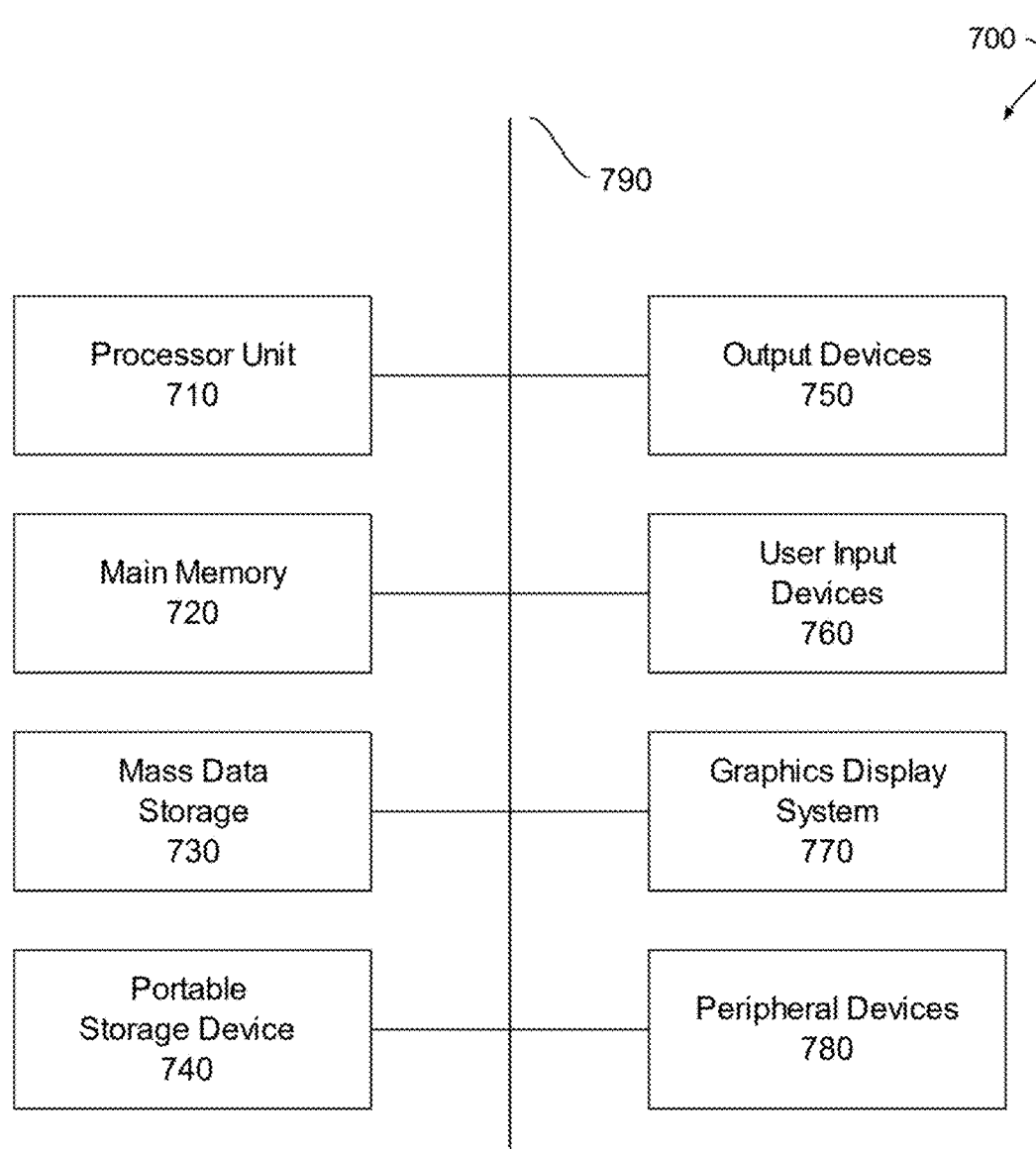
FIG. 7 is a diagrammatic representation of a computing device for a machine, within which a set of instructions for causing the machine to perform any one or more of the methodologies discussed herein can be executed.

FIG. 7 illustrates a computer system 700 that may be used to implement embodiments of the present disclosure, according to an example embodiment. The computer system 700 may serve as a computing device for a machine, within which a set of instructions for causing the machine to perform any one or more of the methodologies discussed herein can be executed. The computer system 700 can be implemented in the contexts of the likes of computing systems, networks, servers, or combinations thereof. The computer system 700 includes one or more processor units 710 and main memory 720. Main memory 720 stores, in part, instructions and data for execution by processor units 710. Main memory 720 stores the executable code when in operation. The computer system 700 further includes a mass data storage 730, a portable storage device 740, output devices 750, user input devices 760, a graphics display system 770, and peripheral devices 780. The methods may be implemented in software that is cloud-based.

The components shown in FIG. 7 are depicted as being connected via a single bus 790. The components may be connected through one or more data transport means. Processor units 710 and main memory 720 are connected via a local microprocessor bus, and mass data storage 730, peripheral devices 780, the portable storage device 740, and graphics display system 770 are connected via one or more I/O buses.

Mass data storage 730, which can be implemented with a magnetic disk drive, solid state drive, or an optical disk drive, is a non-volatile storage device for storing data and instructions for use by processor units 710. Mass data storage 730 stores the system software for implementing embodiments of the present disclosure for purposes of loading that software into main memory 720.

The portable storage device 740 operates in conjunction with a portable non-volatile storage medium, such as a floppy disk, a CD, a DVD, or a USB storage device, to input and output data and code to and from the computer system 700. The system software for implementing embodiments of the present disclosure is stored on such a portable medium and input to the computer system 700 via the portable storage device 740.

User input devices 760 provide a portion of a user interface. User input devices 760 include one or more microphones, an alphanumeric keypad, such as a keyboard, for inputting alphanumeric and other information, or a pointing device, such as a mouse, a trackball, stylus, or cursor direction keys. User input devices 760 can also include a touchscreen. Additionally, the computer system 700 includes output devices 750. Suitable output devices include speakers, printers, network interfaces, and monitors.

Graphics display system 770 includes a liquid crystal display or other suitable display device. Graphics display system 770 receives textual and graphical information and processes the information for output to the display device. Peripheral devices 780 may include any type of computer support device to add additional functionality to the computer system.

The components provided in the computer system 700 of FIG. 7 are those typically found in computer systems that may be suitable for use with embodiments of the present disclosure and are intended to represent a broad category of such computer components that are well known in the art. Thus, the computer system 700 can be a PC, handheld computing system, telephone, mobile computing system, workstation, tablet, phablet, mobile phone, server, minicomputer, mainframe computer, or any other computing system. The computer may also include different bus configurations, networked platforms, multi-processor platforms, and the like. Various operating systems may be used including UNIX, LINUX, WINDOWS, MAC OS, PALM OS, ANDROID, IOS, QNX, and other suitable operating systems.

It is noteworthy that any hardware platform suitable for performing the processing described herein is suitable for use with the embodiments provided herein. Computer-readable storage media refer to any medium or media that participate in providing instructions to a central processing unit, a processor, a microcontroller, or the like. Such media may take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a CD Read Only Memory disk, DVD, Blu-ray disc, any other optical storage medium, RAM, Programmable Read-Only Memory, Erasable Programmable Read-Only Memory, Electronically Erasable Programmable Read-Only Memory, flash memory, and/or any other memory chip, module, or cartridge.

In some embodiments, the computer system 700 may be implemented as a cloud-based computing environment, such as a virtual machine operating within a computing cloud. In other embodiments, the computer system 700 may itself include a cloud-based computing environment, where the functionalities of the computer system 500 are executed in a distributed fashion. Thus, the computer system 700, when configured as a computing cloud, may include pluralities of computing devices in various forms, as will be described in greater detail below.

In general, a cloud-based computing environment is a resource that typically combines the computational power of a large grouping of processors (such as within web servers)

and/or that combines the storage capacity of a large grouping of computer memories or storage devices. Systems that provide cloud-based resources may be utilized exclusively by their owners or such systems may be accessible to outside users who deploy applications within the computing infra-structure to obtain the benefit of large computational or storage resources.

The cloud may be formed, for example, by a network of web servers that comprise a plurality of computing devices, such as the computer system 700, with each server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depends on the type of business associated with the user.

Thus, methods and systems for maximizing the efficiency of an x-ray system have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A non-destructive x-ray imaging detection system, comprising:
    an x-ray source;
    an x-ray sensor;
    a fiber optic faceplate (FOP) to protect the sensor; and
    a field-replaceable scintillator; and
    a data collection and storage device that monitors an open-air signal of the imaging detection system and a signal to noise ratio (SNR) of the imaging detection system at multiple times; wherein;
    a first one of the open-air signals of the imaging detection system and a first one of the SNR of the imaging detection system are compared to successive ones of the open-air signals and SNR to indicate degradation of the field-replaceable scintillator as compared to the x-ray source, thereby providing the user of the imaging detection system an indicator of which element of the system, the field-replaceable scintillator or the x-ray source, needs to be replaced.

2. The detection system of claim 1, wherein:
a threshold level to replace the scintillator is established based on one or more of:
    a signal slope calculated from successive measurements of the open-air signal, conversion gain, and shot noise correlation.

3. The detection system of claim 1, wherein:
the x-ray sensor is a time-delay integration (TDI) sensor.

4. The detection system of claim 1, wherein:
the x-ray sensor is a charge-coupled device (CCD) sensor.

5. The detection system of claim 1, wherein:
the FOP is radiation hardened to mitigate formation of browning centers.

6. The detection system of claim 1, wherein:
the FOP is off-axis relative to the x-ray source.

7. The detection system of claim 1, wherein:
the scintillator is a columnar CsI scintillator.

8. The detection system of claim 7, wherein:
the scintillator is a low afterglow CsI scintillator.

9. The detection system of claim 1, wherein:
a plurality of scintillators are provided on a movable plate, the plate being moved to expose a new one of the scintillators when an original one of the scintillators is determined to be degraded to a point exceeding a preset threshold.

10. The detection system of claim 1, wherein:
scintillator material is formed onto a thin, flexible scintillator film, the scintillator film being wound onto a first supply reel and then fed to a second take-up reel, such that the scintillator film is advanced in stages across the FOP.

\* \* \* \* \*